United States Patent [19]

Charnley

[11] 4,021,865

[45] May 10, 1977

[54] FEMORAL PROSTHESIS

[76] Inventor: John Charnley, Birchwood, Moss Lane, Mere, Knutsford, England

[22] Filed: Aug. 14, 1975

[21] Appl. No.: 604,608

[30] Foreign Application Priority Data

Aug. 29, 1974 United Kingdom ............. 37732/74
Sept. 6, 1974 United Kingdom ............. 38965/74

[52] U.S. Cl. ............................. 3/1.913; 128/92 CA
[51] Int. Cl.² ........................................... A61F 1/24
[58] Field of Search ........................... 3/1.9–1.913, 3/1; 128/92 C, 92 CA

[56] References Cited

UNITED STATES PATENTS

| | | | |
|---|---|---|---|
| 3,466,670 | 9/1969 | Christiansen | 3/1.913 |
| 3,658,056 | 4/1972 | Huggler et al. | 3/1.912 X |
| 3,685,058 | 8/1972 | Tronzo | 3/1.912 |
| 3,848,273 | 11/1974 | Frey | 3/1.913 |

*Primary Examiner*—Ronald L. Frinks
*Attorney, Agent, or Firm*—Ross, Ross & Flavin

[57] ABSTRACT

When a femoral prosthesis, mounted in the femur, by cement, has been in use for some years, the upper part thereof can become unsupported and fracture of the stem near its mid-point can occur. To minimize this possibility, a flange is provided on at least one side of the stem of the prosthesis to ensure better load transfer to the cement and thus the bone. To prevent shear forces causing such separation at the concave surface of the stem of the prosthesis, this can be provided with serrations to discourage separation.

9 Claims, 9 Drawing Figures

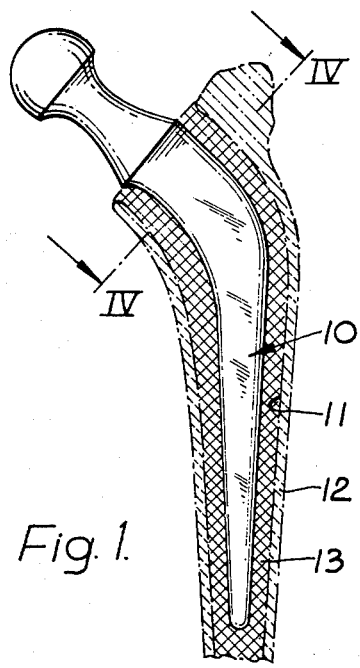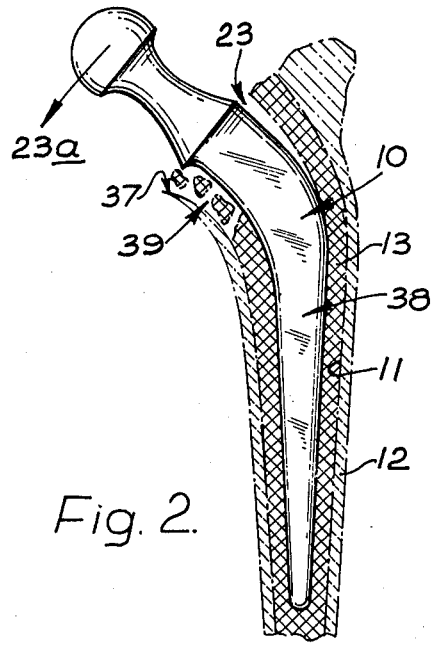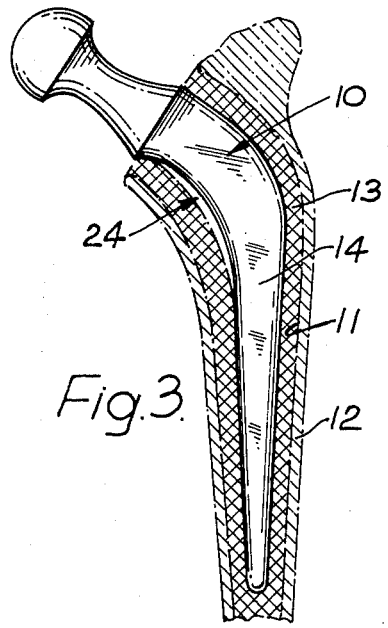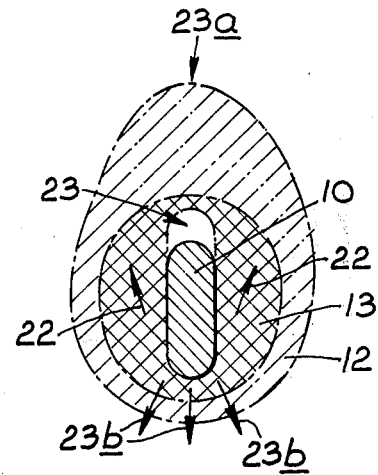

FEMORAL PROSTHESIS

This invention relates to a femoral prosthesis for use in an artificial hip joint.

Since the introduction into hip surgery of acrylic cement for the purpose of bonding the stem of a femoral head prosthesis into the medullary cavity of the upper end of the femur (FIG. 1), it is not uncommon experience for the stem of the prosthesis to fracture about its mid-level after a number of years in service, especially in the case of heavy patients. Before cement was used, the load of the weight of the body was transferred to the bones of the femur mainly through the cut end of the upper end of the femur through the medium of a collar provided on the prosthesis for this purpose. As bone was absorbed as a result of minute movements taking place between the rigid metal and the more elastic cancellous bone under the influence of fluctuating loads in the course of walking, the whole prosthesis subsided into the medullary canal so that the upper end of the prosthesis retained contact with the bone and transferred load always at the upper levels. When cement is used, an enormous improvement in function is offset by the fact that the femoral prosthesis is not able to subside in the medullary cavity, if bone should absorb in the upper part of the femur, as at 37 in FIG. 2, and the upper half of the prosthesis therefore becomes relatively unsupported (FIG. 2) and becomes a cantilever from the rigidly fixed lower part, with the result that stress is concentrated over a short middle section of the prosthesis leading to fatigue fracture, as indicated at 38 in FIG. 2, at this level. The dimensions of this middle section of the stem of the prosthesis, where this fracture most commonly occurs, are limited by the dimensions of the anatomy of the femue at this level, so that to reduce excessive stress at this level, it is necessary to improve the efficiency of load transmission via the cement from the upper half of the prosthesis to the bone in the upper part of the femur.

Defective support by the cement between the concave, medial, surface of the upper half of a prosthesis and the corresponding part of the femur (the calcar femoris) may result from splitting or fracturing of the cement under high local stresses (FIG. 2) and this is a tendency in designs presenting narrow, or wedge-shaped sections to the cement at this point, but there is a limit to the total area on this concave surface of the stem which can transfer load to the cemment as a consequence of the anatomy of the bone. Attempts to use the anterior and posterior surfaces of the stem for load transference to the cement, as for instance by providing these surfaces with ridges or various types of rough projections, have the serious disadvantage of making it impossible to extract the metal prothesis from the cement bed should this ever become necessary.

The cement adjacent the upper half of the stem of the prosthesis is not so well able to support the prosthesis, because at this level, the femur is expanded in a trumpet form and, because the prosthesis is curved away from the central axis, the bone cannot contribute to supporting the cement symmetrically and equally on all sides (FIG. 1). The curved prosthesis deflects under load (FIG. 3) and there is a tendency for the cement in contact with its concave surface not to follow the change in curvature; when the concavity of the metal part increases (radius of curvature decreasing), the curvature of the cement tends to stay at its original radius with the result that a shearing movement takes place between the metal and the cement, which movement is favoured by the smoothness of the surfaces and the absence of adhesion between them.

The result of this is, of course, that again the prosthesis becomes relatively unsupported over its upper half.

The present invention seeks to avoid high stress concentration at middle levels of the prosthetic stem by making the cement in the upper half of the medullary cavity more efficient in accepting loads from the prosthesis, and to do this without interfering with easy removal of the prosthesis, should this becomes necessary once the cement is hard.

According to the invention, there is provided a femoral prosthesis comprising a head support by a neck which projects from an upper end of a stem having an upper curved portion, defined by a curved bottom surface, an opposed convexly curved top surface and opposed side walls therebetween. Also there is provided at least one lateral flange extending outwardly from a convex surface of the stem, the flange being operative, when the prosthesis is mounted in a femur by cement, to transmit loads applied to the prosthesis more effectively to the cement surrounding, and thus to the bone surrounding, the upper portion of the prosthesis.

A flange can be provided on both sides of the stem and the flanges on opposite sides of the stem can be of different lengths to facilitate insertion of the prosthesis into a femur having an asymmetrically arranged medullary cavity. The surface of the flanges adjacent the sides of the stem can lie at 90° to the sides of the stem, but advantageously can be arranged to lie at an angle of less than 90° to the sides of the stem and can be concave so that pressure on the prosthesis does not effect a bursting force on the cement, but tends to draw the cement closer to the stem. To reduce or obviate the possibility of the aforementioned shearing movement causing the prosthesis to become unsupported, the prosthesis preferably has serrations on a concavely curved upper portion of the stem thereof.

Preferably the serrations are in the forms of steps and are so directed that they do not lock with surrounding cement, should withdrawal of the prosthesis from a femur be necessary.

The invention will be described further, by way of example, with reference to the accompanying drawings, wherein:

FIG. 1 is a cross-sectional view through an upper part of a femur provided with a conventional femoral prosthesis;

FIG. 2 is a view similar to that of FIG. 1 but illustrating (in an exaggerated manner) how the upper part of the prosthesis can become unsupported on the concave side and so separate from cement on the convex side;

FIG. 3 is a view similar to that of FIG. 1 but illustrating, in an exaggerated manner, how the stem of a prosthesis can bend under load, and a gap appear between the stem and the cement to leave the upper half relatively unsupported;

FIG. 4 is a fragmentary cross-section on the line IV—IV of FIG. 1;

Figure 5:
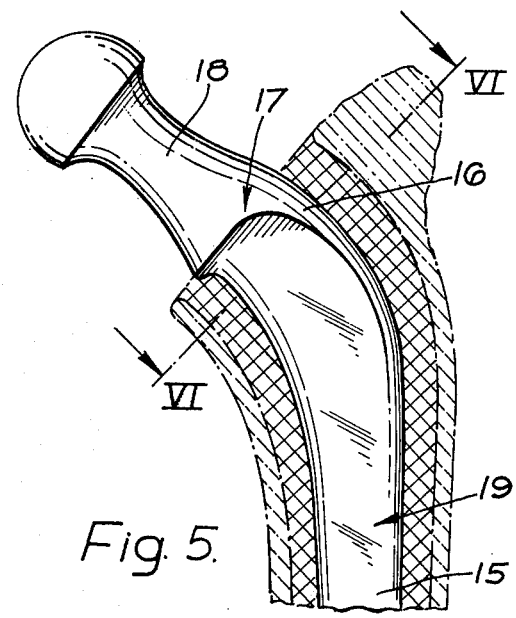
FIG. 5 is a view similar to that of FIG. 1, the femur accommodating a first preferred embodiment of femoral prosthesis conforming to the invention.

FIG. 1 illustrates a conventional prosthesis 10 mounted in the medullary cavity 11 of a femur 12 by means of acrylic cement 13. FIG. 2 illustrates, in an exaggerated manner, how the prosthesis 10 can become unsupported at its upper end by fragmentation of the cement 13 at 39, (FIG. 2) due to the patient's weight causing movement of the stem in the direction of the arrow 23a (FIG. 4) and separation of the prosthesis from the cement at 23. This force is spread over a relatively small area of the cement 13 as shown by the small arrows 23b in FIG. 4.

As can be seen from FIG. 3, the conventional prosthesis 10, affixed in the medullary cavity 11 of a femur 12 by means of cement 13 can deflect under load (the deflection is exaggerated in the figure) and a shearing movement occurs between the concave surface of metal of the stem 14 and the cement 13. As the radius of the upper stem portion decreases, the chord between two points on the metal surface becomes shorter, whereas a corresponding chord on the cement surface tends to remain the same length. The shearing movement is extremely small. The very slight eventual separation, shown exaggerated at 24, can contribute to fragmentation in the highly stressed zone on the concave surface of the prosthesis indicated in FIG. 2 at 39, and so help to cause overloading of the stem 14 and possible fracture at or near its mid point.

Figure 6:
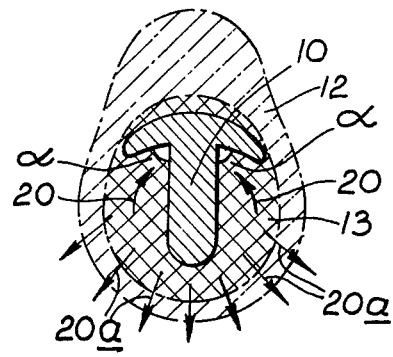
FIG. 6 is a fragmentary cross-section on the line VI—VI of FIG. 5.

A first preferred embodiment of prosthesis 14 (FIG. 5) conforming to the invention has a stem 15 which is basically similar to conventional designs in general shape and dimensions, but has flanges 16 added to the convex side of the prosthesis 14 in its upper part. In its front-to-back dimension, this flange is widest at its junction 17 with the base of the neck 18 of the prosthesis 14 and reduces in width at lower levels to blend into the conventional design of stem at the junction 19 of the upper and middle one thirds, or the upper one-quarter and the distal three-quarters, of the stem. The flanges 16 thus give a T-section to the upper levels of the stem 15 (FIG. 6), the vertical limb of the T representing the body of the stem 15 of the prosthesis 14 and the cross-piece of the T representing the flanges 16. The angle α between the front and back surface of the body of the prosthesis 14 and the flanges 16 is made slightly less than 90°, e.g., 85° to 90°, so that pressure in the direction of arrow 25, on the cement 13 by the prosthesis 14, would not exert a bursting effect on the cement 13 and would tend to pull the cement 13 closer to the front and back surfaces of the stem of the prosthesis as illustrated by the arrows 20. In the conventional prosthesis 10, pressure on the cement in the direction of arrow 23a tends to encourage cement flow as illustrated by the arrows 22 in FIG. 4. The prosthesis 14, because of the flanges 16, spreads the force over the body of the cement as illustrated by the arrrows 20a.

Figure 7:
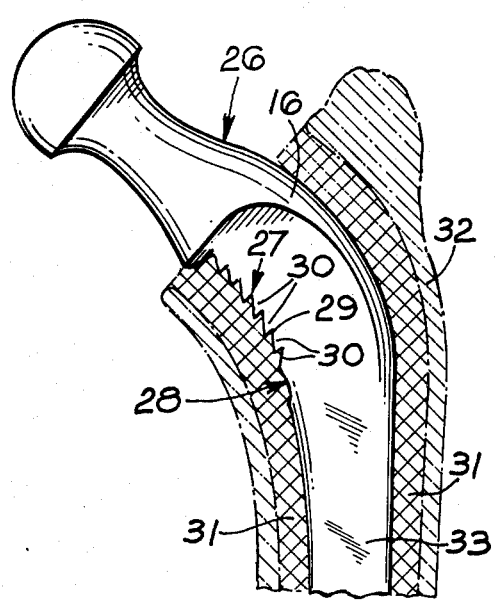
FIG. 7 is a view similar to that of FIG. 5, but showing a second preferred embodiment of femoral prosthesis of the invention.

A second preferred embodiment of prosthesis 26 conforming to the invention is shown in FIG. 7 and differs from prosthesis 14 only in that serrations 27 are provided on its upper concave side 28. These serrations 27 are of saw tooth form steps 29 and the faces 30 of the steps 29 are so disposed that withdrawal of the prosthesis from the cement 31 in a femur 32 is not prevented by the serration 27 forming a key with the cement 31. The serrations 27 have the effect, however, of discouraging shearing motion between the stem 33 of the prosthesis 26 and the cememt 31 in a medullary cavity of a femur.

It might appear advantageous if the stem of the prosthesis 26 were to be provided with serrations, as serrations 27, over the whole of its surface, but against this is the necessity for allowing for extraction of the metal prosthesis from its cement bed in the event of failure of the surgical operation. By confining the serrations to the concave surface of the medial border of the prosthesis 26, which also is the critical area in initiating cleavage from the cement 31 under the deflection cause by load-bearing, no interferenee with ability to extract is incurred, especially if the serrations are shaped stepwise so that one does not interfere with another on extraction, yet offering maximum resistance to shear in the opposite direction.

Figure 8:
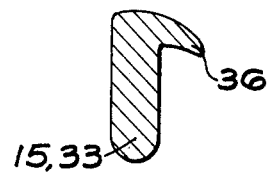
FIG. 8 is a view similar to that of FIG. 6 but showing a first modified prosthesis.
Figure 9:
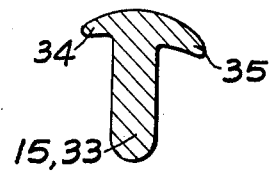
FIG. 9 is a view similar to that of FIG. 6 but showing a second modified prosthesis.

While the T-section offered by a symmetrical disposition of the flanges 16 on the convex border is to be preferred, because of the ability to use the same prosthesis for right and left hips, the use of asymmetrical flanges 34 and 35 (FIG. 9) is possible, one being longer than the other, or for the case where only one flange 36 (FIG. 8) is provided to give an L-shaped section. These asymmetrical flanges would facilitate insertion into femoral cavities which are not symmetrically disposed round the axis of the femur and which would for a symmetrical prosthesis to take up an incorrect position or would demand an excessive amount of bone to be removed to achieve the desired orientation of a symmetrical prosthesis in an asymmetrical medullary cavity.

It is to be noted that the front-to-back thickness of the upper part of the stem of the prosthesis is not increased above that which experience in standard designs has shown convenient for insertion. This means that no excessive enlargement of the cavity in the bone is necessary, as would be necessary to accept the upper half of a stem which is generally thickened in all of its front-to-back dimensions. Moreover, by retaining normal dimensions, there is no reduction in the thickness of the layer of cement between the bone and the front and back surfaces of the prosthesis as would result if the front-to-back dimensions of the metal were generally increased at this level. In the insertion of this new design of prosthesis, increased removal of bone would be required to acccept the flange as it comes in contact with the bone during the very last stages of insertion.

In the insertion of the new prostheses, the standard surgical procedure is adopted in that the prosthesis is forced into the medullary canal after the latter has been tightly packed with cement in the dough state, but in existing designs, the front and back surfaces of the stem merely shear through the soft cement and the volume of cement displaced by entry of the prosthesis escapes unrestrained from the back and sides of the prosthesis. In this improved design however, the escape of cement is restricted by the flange and a final compression force is exerted on the cement when the dorsal flange of the prosthesis commences to come into relation with the bone just before the moment when the collar of the prosthesis finally engages with the cut end of the neck of the femur. This terminal act of the flange, in compressing the cement into a cavity which is progressively being constricted, is considered to be mechanically superior to the state in conventional methods where the free escape of cement continues to the moment when the prosthesis meets the bone and where improvement in contact between cement and prosthesis has to be attempted by manually packing in the cement as a last maneuver.

I claim:

1. A femoral prosthesis comprising: a head supported by a neck projecting from an upper end of a stem having an upper curved portion defined by a curved bottom surface, an opposed convexly curved top surface and opposed side walls therebetween a flange extending laterally outwardly rearwardly from the convex top surface of the stem in a direction generally transverse to said side walls, the flange being operative when the prosthesis is mounted in a femur by cement for transmitting applied loads in a cushioning manner to the cement and bone surrounding the upper portion of the prosthesis.

2. A prosthesis as claimed in claim 1, with the angle between the surface of the flange and the adjacent stem surface being less than 90°.

3. A prosthesis as claimed in claim 1, with the flange being widest at its junction with the neck and tapering to zero.

4. A prosthesis as set forth in claim 1, with the flange length being between one-third and one-quarter of the stem length.

5. A femoral prosthesis comprising: a head supported by a neck projecting from an upper end of a stem having an upper curved portion defined by a curved bottom surface, an opposed convexly curved top surface and opposed side walls therebetween, flanges extending laterally outwardly from each side of the convex top surface of the stem in a direction generally transverse to said side walls, the flanges being operative when the prosthesis is mounted in a femur by cement for transmitting applied loads in a cushioning manner to the cement and bone surrounding the upper portion of the prosthesis.

6. The prosthesis as set forth in claim 5, the flanges being of equal size for allowing use of the prosthesis for both left and right femurs.

7. In the prosthesis as set forth in claim 5, with the flanges being of different sizes for allowing use of the prosthesis in a femur having an asymmetrical medullary cavity.

8. A femoral prosthesis comprising: a head supported by a neck projecting from an upper end of a stem having an upper curved portion, lateral flange extending outwardly from each side of the convex surface of the stem, the flanges being operative, when the prosthesis is mounted in a femur by cement, to transmit loads applied to the prosthesis more effectively to the cement surrounding and thus to the bone surrounding, the upper portion of the prosthesis, the flanges being of different sizes to enable the prosthesis to be used in a femur having an asymmetrical medullary cavity.

9. A femoral prosthesis comprising: a head supported by a neck projecting from an upper end of a stem having an upper curved portion, a flange extending laterally outwardly from a convex surface of the upper curved portion of the stem, the flange in its front-to-back dimension, being widest at its junction with the base of the neck and reducing in width at lower levels for blending into the stem, the body of the stem representing the vertical lines of a T-section and the flange representing the cross-piece of the T-section.

* * * * *